(12) United States Patent
Pfeiffer et al.

(10) Patent No.: US 10,485,432 B2
(45) Date of Patent: Nov. 26, 2019

(54) METHOD FOR DETERMINING BLOOD PRESSURE IN A BLOOD VESSEL AND DEVICE FOR CARRYING OUT SAID METHOD

(71) Applicant: PHILIPS MEDIZIN SYSTEME BÖBLINGEN GMBH, Böblingen (DE)

(72) Inventors: Ulrich Pfeiffer, Munich (DE); Reinhold Knoll, Neuburg (DE)

(73) Assignee: PHILIPS MEDIZIN SYSTEME BÖBLINGEN GMBH, Böblingen (DE)

( * ) Notice: Subject to any disclaimer, the term of this patent is extended or adjusted under 35 U.S.C. 154(b) by 540 days.

(21) Appl. No.: 15/301,759

(22) PCT Filed: Apr. 4, 2014

(86) PCT No.: PCT/EP2014/000905
§ 371 (c)(1),
(2) Date: Oct. 4, 2016

(87) PCT Pub. No.: WO2015/149822
PCT Pub. Date: Oct. 8, 2015

(65) Prior Publication Data
US 2017/0112396 A1    Apr. 27, 2017

(51) Int. Cl.
*A61B 5/02*    (2006.01)
*A61B 5/021*    (2006.01)
*A61B 5/00*    (2006.01)
*A61B 5/022*    (2006.01)
*A61B 5/024*    (2006.01)

(52) U.S. Cl.
CPC .......... *A61B 5/02125* (2013.01); *A61B 5/022* (2013.01); *A61B 5/6824* (2013.01); *A61B 5/7239* (2013.01); *A61B 5/02416* (2013.01); *A61B 2560/0238* (2013.01); *A61B 2562/043* (2013.01)

(58) Field of Classification Search
CPC ..................................................... A61B 55/00
See application file for complete search history.

(56) References Cited

U.S. PATENT DOCUMENTS

| | | | |
|---|---|---|---|
| 4,907,596 A | 3/1990 | Schmid et al. | |
| 5,309,916 A | 5/1994 | Hatschek | |
| 6,475,153 B1 | 11/2002 | Khair et al. | |
| 6,533,729 B1* | 3/2003 | Khair | A61B 5/021 600/480 |
| 7,029,447 B2 | 4/2006 | Rantala | |
| 2010/0298650 A1* | 11/2010 | Moon | A61B 5/0002 600/301 |
| 2011/0288419 A1* | 11/2011 | Baruch | A61B 5/02125 600/485 |
| 2012/0065526 A9 | 3/2012 | Kopetsch et al. | |
| 2012/0108928 A1* | 5/2012 | Tverskoy | A61B 5/0059 600/324 |
| 2013/0079648 A1 | 3/2013 | Fukuzawa et al. | |
| 2013/0211208 A1 | 8/2013 | Varadan et al. | |

FOREIGN PATENT DOCUMENTS

| | | |
|---|---|---|
| JP | H4250135 A | 9/1992 |
| JP | H10201724 A | 8/1998 |
| JP | 2014000105 A | 1/2014 |
| WO | WO-2014114423 A1 | 7/2014 |

* cited by examiner

*Primary Examiner* — Joel F Brutus (57) ABSTRACT

The invention relates to a method for determining blood pressure in a blood vessel, according to which a pulse wave propagation time is caluculated in a measuring operation by means of at least two sensors arranged at a defined distance from one another. The method is characterized in that the blood pressure is calculated using a calibration carried out by means of a compression pressure measurement.

16 Claims, 3 Drawing Sheets

METHOD FOR DETERMINING BLOOD PRESSURE IN A BLOOD VESSEL AND DEVICE FOR CARRYING OUT SAID METHOD

CROSS-REFERENCE TO RELATED APPLICATION

This patent application claims priority to international application No. PCT/EP2014/000905, filed Apr. 4, 2014, the entire content of which is incorporated herein.

BACKGROUND OF THE INVENTION

When measuring the arterial blood pressure, the pressure in an arterial blood vessel of a human being or an animal is measured. In medical diagnosis it plays a key role for a large number of illnesses, in particular of the cardiovascular system.

Furthermore, the direct, invasive measurement of blood pressure by means of a pressure sensor having a direct hydraulic connection with the blood in a blood vessel is distinguished from the indirect, non-invasive measurement of blood pressure which is usually carried out at one of the extremities with the aid of a pneumatic cuff.

In the case of direct measurement, a blood vessel, mostly a peripheral artery, is punctured, and a catheter inserted. The latter is connected to a pressure sensor via a tube filled with liquid, through which the arterial blood pressure curve can be displayed on a monitor. The measurement is exact, and offers the benefit of continual monitoring, as long as it is guaranteed that an ongoing column of liquid between the blood vessel and the pressure sensor, not containing any blood clot or air bubble, exists, and the pressure hose has the necessary stiffness, which is not always a given in clinical practice. In addition, the heart rate, the systolic, diastolic and mean arterial blood pressure (SAP, DAP, MAP) and the pulse pressure variation (PPV), as well as—by means of the pulse contour method—the cardiac output (PCCO) and the stroke volume variation (SVV) can be determined. Since the method is time-consuming and invasive, it causes considerably increased costs and is associated with the risk of bleeding, hematomas, thromboembolisms, infections and nerve injuries. It is especially utilized for monitoring purposes during an operation, in intensive care units and in the cardiac catheter laboratory, however usually not outside the scope of these applications.

With indirect arterial pressure measurement, the arterial pressure is measured at one of the extremities, mostly on the arm, with the aid of a blood pressure monitor. Although indirect measurements are not as precise as direct measurements of the blood pressure, the light, rapid, safe and cost-effective implementation makes them the means of choice with most medical applications. The manual or automated measurement may be performed auscultatorily, on palpation and oscillatorily.

In the case of the auscultatory measurement, a pneumatic pressure cuff is inflated on the upper arm up to above the anticipated arterial pressure. When the cuff pressure is slowly lowered, the occurrence, and thereafter the disappearance again of so-called "Korotkoff sounds" can be heard above the artery of the arm with the aid of a stethoscope. The value which can be read off on the scale of the manometer when acoustically perceiving the Korotkoff sounds for the first time corresponds to the upper, systolic blood pressure. The systolic blood pressure is, at this moment, greater than the pressure in the cuff. The pressure in the cuff is further reduced with a suitable speed. Should it fall short of the diastolic arterial pressure, the Korotkoff sounds disappear. This value corresponds to the diastolic blood pressure. The auscultatory measurement still serves as a reference procedure in the case of non-invasive measurement procedures.

Also in the case of measurement on palpation, a pressure cuff is placed on the upper arm. When the cuff pressure is reduced again, the pulse is felt at the radial artery. The value which can be read off on the scale of the measuring device when feeling the pulse for the first time corresponds to the systolic blood pressure. The diastolic blood pressure cannot be determined in this way. The method is in particular used for an application in a loud environment or if no stethoscope is to hand.

With the oscillatory measurement, the artery in the upper arm or wrist or leg is pressed with the aid of a pressure cuff. While the air is slowly being let out of the pressure cuff, the blood begins to flow through the artery again. In the process, vibrations in the arterial walls, which are triggered by the flow of blood beginning, can be recorded. Such vibrations, also known as oscillations, first become stronger, then weaker, and finally fade out altogether once the blood flows through the blood vessels again. The vibrations are transmitted to the pressure cuff, and in this way lead to an oscillating needle deflection of the manometer. The maximum and minimum values of the needle deflection chronologically correspond to the systolic and diastolic blood pressure. From the cuff pressure at the point in time of the maximum oscillations and the full width at half maximum, the systolic and diastolic pressure can be calculated. When performing a manual measurement, only imprecise results are achieved with this method. This method is, however, utilized in automatic blood pressure measurement devices, in particular also with permanent monitoring, e.g. intraoperatively and/or postoperatively, in the recovery room. This involves that, as an alternative to the continuous invasive pressure measurement, the blood pressure measurement devices measure the arterial blood pressure of the patient intermittently, at intervals of a few minutes. When measuring the vibrations determined electronically, the systolic and diastolic blood pressure are calculated mathematically, with the help of an algorithm, from the curve progression of the vibrations.

According to EP 0 467 853 B1, it is disclosed in the publication, "Possible determinants of pulse wave velocity in vivo", Masahiko Okada, IEEE Transactions on Biomedical Engineering, Vol. 35, No. 5, May 1988, pp. 357 to 361, that a certain correlation between the pulse wave velocity and the systolic and diastolic blood pressure can be noticed. Such a weak, low correlation is, however, according to this teaching, said to not make it possible to determine the blood pressure.

On this basis, a method of continuously determining the blood pressure of a patient is proposed in EP 0 467 853 B1, in the case of which, using an electronic measuring device, which contains two sensors, arranged at a defined distance, at least one factor which changes chronologically with the beat of the pulse, is determined, which is a measure of the flow velocity, the flow rate, the volume of the arterial blood or the cross-sectional area of outlet orifice flow of an arterial blood vessel, and a second factor is determined, which is a measure of the pulse wave velocity of a pressure wave in the blood in said blood vessel caused by a heartbeat. The blood pressure is obtained by means of both factors, taking calibration values into account. In that respect, it could, for example, be made use of the fact that the blood pressure is proportional to the flow velocity of the blood. The quotient "kv/r2" serves, in that regard, as a proportionality factor, wherein "kv i" s a constant, and "r" the radius of the vessel section observed (assuming a circular cross section). Were "r" a constant, the blood pressure could be determined directly from multiple measurements of the flow velocity. As the vessel wall is, however, elastic, and "r" is accordingly not constant, but highly variable, it is necessary to include the measurement of the pulse wave velocity into the formula. In that respect, use is made of the fact that the module of elasticity of the vessel wall can be determined from the pulse wave velocity.

The functionality of the sensors in the case of the method disclosed in EP 0 467 853 B1 may be optically based. To this end, they may each have an optoelectronic transformer, serving as a spotlight, e.g. a laser light-emitting diode, and an optoelectronic transformer serving as a light receptor, such as a photodiode. Both sensors may be integrated into a cuff and attached to one of a patient's forearms, for example, in order to ascertain the blood pressure. A calibration of the sensor-based determination of the blood pressure can, in line with a conventional, non-invasive method according to Riva-Rocci, be performed with an inflatable cuff. The latter involves the cuff being placed at a different extremity of the patient than is stipulated for the sensor cuff, to avoid the sensor-based measurements being falsified. Calibration can be undertaken once at the beginning of the sensor-based long-duration measurement, or repeatedly, after a respective defined period of time, such as daily.

US 2013/0079648 A1 discloses a method and a device for measuring the pulse wave velocity in a vein, wherein a bulging out of the vein below the sensors induced by pressure is detected underneath the sensors using two pressure sensors that are integrated into a cuff, for example, at a defined short distance. The pulse wave transit time can be determined by means of sensors, if, for instance, the time difference of the ascertaining of a pressure maximum allocated to the same pulse wave is drawn upon by the two sensors. From the pulse wave transit time, a conclusion can then be drawn about the pulse wave transit time in connection with the known distance between the sensors.

In US 2013/0079648 A1 it is, moreover, disclosed that a conclusion can also be drawn about the blood pressure based on the (two) pressure sensors. This involves that the respective voltage of the two pressure sensors that is measured is converted into a value for the blood pressure based on a transformation coefficient matrix. The average value from the two values of the two pressure sensors is then taken to be the value determined for the blood pressure. Since the transformation coefficient matrix is generally not known, and can change over time, this method is practically not implementable.

SUMMARY OF THE INVENTION

Taking this prior art as a starting point, the task forming the basis for the invention was to specify a method, that can be implemented in the simplest way possible in terms of the technical design, is easy to apply and/or does not impair the patient for continuously measuring the blood pressure in a non-invasive manner.

This task is resolved by means of a method in accordance with certain embodiments described herein. A device for carrying out such a method is also described. Advantageous embodiments of the method and advantageous embodiments of the device can be seen from the description of the invention below.

The method in accordance with the invention is based on the awareness that, although the correlation between the pulse wave velocity and the blood pressure described in EP 0 467 853 B1 is designated too weak to be able to determine the blood pressure from it, it is nevertheless made possible to determine the blood pressure from it. Contrary to the method described in EP 0467 853 B1, the method in accordance with the invention does not require any signal that is in proportion to the flow velocity. Any signal changing synchronously with the pulse rate is sufficient. It has, namely, been recognized that the change in the pulse wave transit time may be deemed at least functionally dependent upon, and conversely, on certain prerequisites, in the case of changes in the blood pressure pattern that are not too great, to be in proportion to the change in the blood pressure. The average change in the pulse wave transit time can in particular, on certain prerequisites, be considered conversely proportional to the average change in the blood pressure. In particular the change in the pulse wave transit time to the systolic or diastolic point in time may also, on certain prerequisites, be deemed conversely proportional to the systolic or diastolic changes in the blood pressure. The functional connection or the proportionality constant needs to be determined for each test subject or patient, and possibly be re-determined through calibration in the event of greater physiological changes. Advantageously, even multiple changes in the pulse wave transit time, and thus multiple changes in pressure can be determined during a pulse. The current blood pressure is then determined from the original blood pressure determined by means of calibration and the change in the blood pressure This at least functional connection makes a derivation of a quantitative blood pressure pattern from the blood pressure, in particular the diastolic blood pressure (DAP) and/or the systolic blood pressure (SAP) and/or the mean arterial pressure (MAP), possible, in conjunction with a calibration, using at least two quantitative values for the blood pressure, in particular the measurement giving the DAP and/or the SAP, and/or the MAP.

Accordingly, in the case of a method in accordance with the invention to determine the blood pressure in a blood vessel, in the case of which a pulse wave transit time is determined, in a measuring procedure, by means of at least two sensors arranged at a defined distance from one another, it is stipulated that the blood pressure is determined by a calibration from the change in the pulse wave transit time. The calibration can, in the simplest case of the inversely proportional dependence be undertaken with at least two known pressure values, for instance with the mean pressure and the diastolic pressure from a clamping pressure measurement.

A clamping pressure measurement is understood to mean a method in the case of which a pressure cuff placed on an extremity of the human being or animal whose blood pressure is supposed to be determined (in particular by inflating the pressure cuff), a pressure is exerted on the corresponding section of the extremity, which is initially selected to be sufficiently great that a flow of blood through the blood vessel observed in this section of the extremity is interrupted. The pressure applied using the pressure cuff is subsequently reduced in a controlled manner, and the blood pressure (pattern) is concluded from procedures occurring in the process. Conversely, conclusions about the blood pressure (pattern) can also already be drawn during the inflation of the pressure cuff undertaken at a constant or varying speed. For example, the auscultatory clamping pressure methods and clamping pressure methods on palpation in accordance with the invention already described can be used for calibration. Preferably, the oscillatory clamping pressure method already described is used, as, preferably, a fully automatic evaluation of the measurement readings obtained in the process and the use of them for calibrating the sensor-based measurements is supposed to take place.

When carrying out the method in accordance with the invention, in particular also when the prerequisites of the inversely proportional dependence are no longer fulfilled, it can, moreover, be stipulated that a pulse curve form (i.e. the course of the blood pressure across a heartbeat) derived from the clamping pressure measurement is used, in order to determine a transfer function. The transfer function is obtained by folding back a measured sensor signal with the pulse curve signal known from other methods of measurement. By means of this transfer function, a pulse curve form can be determined, with subsequent measurements, through folding, without a pulse curve known from another method of measurement from the path of the signals obtained by means of the sensors. In addition to the latter, the pulse curve form obtained from the signal path can be defined quantitatively within the scope of the calibration.

A preferred method of determining a pulse curve form, taking as a starting point a clamping pressure measurement, is disclosed in International Patent Application PCT/EP2014/000031. This method is based on recording multiple pulse curves with different constant clamping pressures or continuously increasing or falling clamping pressure, in regard to which every pulse curve is weighted with a function dependent upon the clamping pressure. The sum of the weighted pulse curves can then be assumed to be a good approximation of the unscaled invasive blood pressure pattern, i.e. the pulse curve form of relevance in this case. The weighting can preferably be undertaken according to the difference between the invasive blood pressure and the clamping pressure, wherein an estimated value for the invasive blood pressure can be used as an initial value for carrying out the procedure. The entire content of PCT/EP2014/000031 is adopted to form part of the content of the present description, by making reference to it.

This determination of a pulse curve form by means of a previously determined transfer function can thus in particular also be undertaken if precisely no clamping pressure measurement is performed. Accordingly, it can preferably be stipulated that multiple measuring procedures are performed, wherein calibrations are always only undertaken after several (respective) measuring procedures have been performed. An advantage of the method in accordance with the invention is that the calibration, that is preferably performed by means of a clamping pressure measurement, does not need to be undertaken for each measuring procedure, but the measurement readings arising therefrom can be used to calibrate multiple measuring procedures. That means that the blood pressure can be determined continuously, by means of the sensors, whereas a pulse curve form that is drawn upon to calibrate the sensor-based measurement readings, and is in particular obtained through a clamping pressure measurement, is only obtained intermittently. The period of time between every two calibration measures can be variably selected. It is, in that respect, to be borne in mind that a relatively frequent calibration can improve the precision of the sensor-based determination of the blood pressure between the clamping pressure measurements, however, due to the clamping pressure to be applied to an extremity of the conscious patient for a brief period of time (when performing a clamping pressure measurement), it is usually perceived as being less pleasant, or even unpleasant. The calibration measurements should therefore be undertaken as seldom as possible, but frequently enough as is necessary to achieve a sufficient degree of precision. It may, for example, be stipulated to carry out calibration measurements at intervals of two to fifteen minutes, for instance at intervals of approx. five or approx. 10 minutes. Naturally, it is also possible to stipulate the periods of time between every two respective successive calibration measurements to be of different lengths or for a series of successive calibration measurements to be carried out at variable intervals.

In a preferred embodiment of the method in accordance with the invention, it may be stipulated that the pressure curve or the pulse wave be determined optically. In that respect, light pulses can in particular be emitted in the direction of the blood vessel, (always) using an illuminant of the sensors, wherein a portion of the light pulses reflected by the blood in the blood vessel and/or a portion of the light pulses (or a change in the same) transmitted by the blood in the blood vessel is detected using a detector of the sensors. Fluctuations in the area of the heart rate of the measurement signal path of said at least two sensors detected can, in the process, be allocated to the blood pressure changing locally. The use of intermittent illuminants and detection in the activated and non-activated state of the illuminant allows, in a customary manner, for separating error signals, such as extraneous light.

A device for carrying out a method in accordance with the invention comprises at least the sensors, a pressure cuff for performing the clamping pressure measurement and an evaluation unit, wherein the sensor unit and, if applicable, also the evaluation unit, is/are integrated into the pressure cuff. A compact technical design of the device in accordance with the invention, as well as no-fuss handling, may result. What may be problematic, in that respect, in certain circumstances, is the relatively small distance between said at least two sensors, leading to a correspondingly short pulse wave transit time (to be determined).

In particular in order to be able to continuously measure short pulse wave transit times with sufficient precision, it may be stipulated in a preferred embodiment of the method in accordance with the invention that a time offset between the activation (i.e. the emission of a light pulse and the detection of a reflected and/or transmitting portion of said light) of said at least two optical sensors (i.e. an activation of a first of the (upstream) sensors and the successive, time-offset activation of the second sensor) is regulated in such a way (especially continuously) that measurement readings that are as similar in relation o one another as possible are achieved for both sensors, and the time offset accordingly largely corresponds to the pulse wave transit time. In that respect, measurement readings that are similar "in relation to one another" should be understood to mean that they essentially show the same place in the comparable measurement value trends in regard to the curve form. The same "relative" measurement readings can, actually, constitute different absolute measurement readings. This can, in particular, be due to the fact that, because of the different positioning of said at least two sensors (and the thus possibly accompanying different distance from the respective section of the blood vessel observed and/or the different technical design of the tissue located between the two sensors and the corresponding blood vessel sections), also in the case of light pulses being emitted by the two sensors that are of the same strength, different-sized reflected and/or transmitted portions are detected. These measurement value trends that differ in regard to the absolute values may make it expedient to standardize them beforehand.

In order to simplify the adjustment of the time-offset activation of the two sensors, it may be stipulated that the (respective) time delay is determined based on characteristic, and thus easily identifiable, and therefore easily comparable, values of the measurement value trends. In particular the minimum values (which may correspond to the diastolic blood pressure to be obtained from the latter) and maximum values (which may correspond to the systolic blood pressure to be obtained from the latter) and/or the places showing the maximum increase in the measurement readings can be drawn upon as characteristic values.

The time offset can essentially be controlled, whether analog or digital, for example with a resolution of between 3 and 15 ns, in particular 5 ns.

In order to determine any adjustment deviation of the time offset for an impending measurement procedure, the time delay between determining the same characteristic value of the measurement value trends determined by the sensors in a preceding measurement procedure can be used. It can preferably be stipulated that the delay is constantly controlled retrospectively, so that the measurement value trends obtained by said at least two sensors are always to a large extent the same except for precisely this delay.

A duration of, for example approx. 1 ms, that remains constant can be stipulated for the light pulses emitted by the sensors (at least within a given measuring procedure). It may, however, be advantageous if, in phases of an increase in the measurement readings, the duration of the light pulses is extended in comparison to phases of a drop in the measurement readings. In connection with a detection of the reflected and/or transmitted portion of the light per light pulse during an increase in the measurement reading that is repeated or lasts longer (than in the other phases), which is further preferred, the highest possible resolution can thereby be achieved without any extensive expenditure of energy and illegitimate heating of the sensors while the measurement readings are increasing, and thus during that section of the individual measurement value trends which preferably comprise the characteristic values preferably used to determine the time offset. A chronological distortion of the measurement readings over the time, and, in certain circumstances, also the measurement value amplitudes may in fact thereby result, which is not, however, a hindrance to evaluating the measurement value trends in accordance with the invention. On the contrary, advantageously, especially relevant phases of the measurement value trends (the characteristic values observed) can, as a result, be accorded more weight.

Furthermore, in order to give as high a resolution as possible, chronologically, to the rapid change in the signal caused by the systolic rise in pressure, it can, in turn, be stipulated in a preferred embodiment of the method in accordance with the invention that, in order to ascertain measurement readings, it is not necessary to wait until transient responses in the detectors have been terminated, and therefore essentially constant measuring signal values can be read off. Rather, the measurement readings are determined based on evaluating the transient responses (any respective section), in particular by ascertaining the maximum increase and/or the integral of the measurement signal path.

In a further preferred embodiment of the method in accordance with the invention, it may be stipulated that the measurement of the blood pressure that has been taken by means of a clamping pressure measurement is not only drawn upon to calibrate the sensor-based measurement procedures, but, conversely, the measurement of the blood pressure using a clamping pressure measurement is likewise improved by the sensor-based measurement procedure performed simultaneously. Accordingly, it may also be stipulated that sensor-based measurement value trends are determined during the calibration measurement, and a pressure curve determined by means of the calibration measurement is controlled on the basis of these measurement value trends is controlled.

Through the integration of the sensor unit into the pressure cuff, the former can be used advantageously in order to, keep the sensors safe, and in particular with a defined contact force at the intended places of the extremity used to determine the blood pressure also at those times when no clamping pressure measurement is undertaken. In addition, it may be stipulated that if no clamping pressure measurement is undertaken, a holding clamping pressure is applied within the pressure cuff. This holding clamping pressure is preferably selected in such a way that the holding function is fulfilled, while simultaneously, however, any influencing of the venous reflux in the blood vessels is kept minor or is avoided. For example, the holding clamping pressure may amount to approx. 5 to 20 mm Hg, in particular 10 mm Hg.

In order to get as identical a transient response as possible for the measuring signals for said at least two sensors, it may preferably be stipulated that the two sensors have a common detector or two detectors connected in parallel.

BRIEF DESCRIPTION OF THE INVENTION

In order to shield the detector of a sensor as much as possible from extraneous light, it may, moreover, be stipulated that the latter is placed between the illuminant of the corresponding sensor and a longitudinal axis of the pressure cuff aligned in the circumferential direction of the extremity. In the case of two sensors having been stipulated, the detectors can thus be located between the two outer illuminants.

BRIEF DESCRIPTION OF THE DRAWINGS

The invention is explained in further detail below based on an embodiment shown in the drawings. The following are in the respective case shown schematically in the drawings.

DETAILED DESCRIPTION OF THE INVENTION

Figure 1:
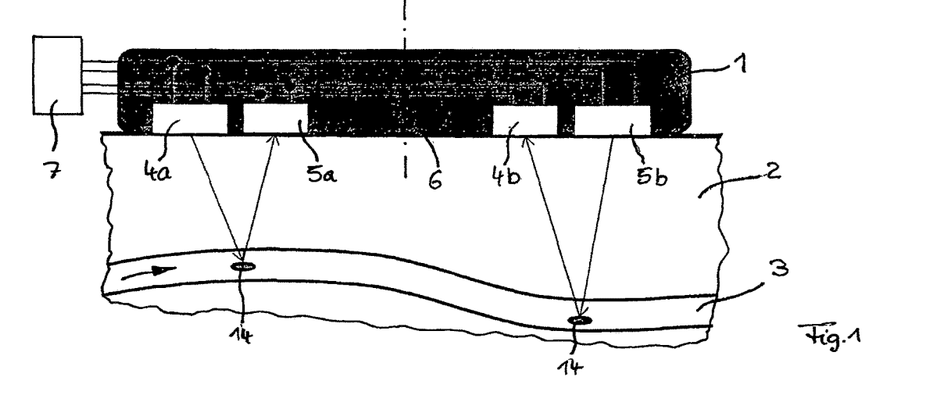
FIG. 1 is a schematic showing use of a device in accordance with the invention.

FIG. 1 shows a device in accordance with the invention for determining the blood pressure in a blood vessel, for example an artery of a human being or an animal, schematically. The device comprises a pressure cuff 1, which can be placed around an extremity 2, for example an upper arm of a human being. The pressure cuff 1 can be variably filled with a fluid, for example air, whereby the former expands.

The associated reduction in size of the free internal cross-section of the pressure cuff 1 leads to a radial compression of the section of the extremity 2 located therein, and thus to clamping pressure being exerted upon a section of an artery 3 running in this section of the extremity 2. A clamping pressure measurement is performed at more or less regular intervals, in a customary way, using the pressure cuff 1. This then serves to determine a transfer function, as well as the calibration of sensor-based measurements of the pulse wave transit time and a pulse curve form of the blood pressure determined therefrom using the transfer function. The clamping pressure measurement can, for example, be implemented as an oscillatory measurement, which serves to measure changes in pressure that are generated when the internal pressure is specifically lowered through a blood flow occurring in the artery and the resulting vibrations generated thereby, using a pressure sensor (not shown) that measures the internal pressure of the pressure cuff 1. Based on these changes in pressure, the quantitative course of the pulse curve can be determined in a customary manner.

Figure 5A:
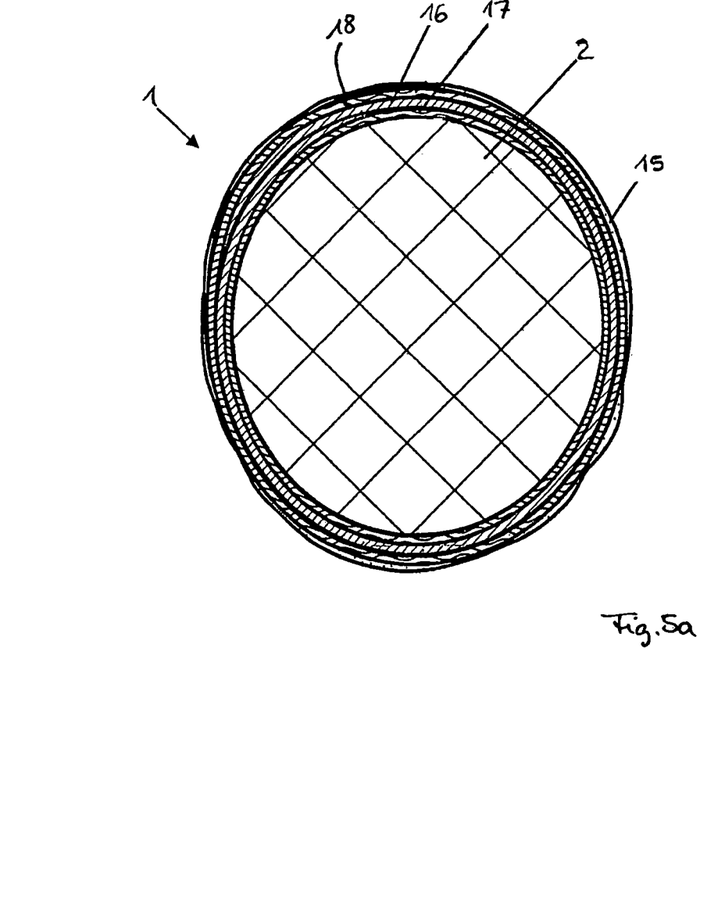
FIG. 5a graph showing embodiment of a pressure cuff of the device in accordance with FIG. 1 in an unfilled state.
Figure 5B:
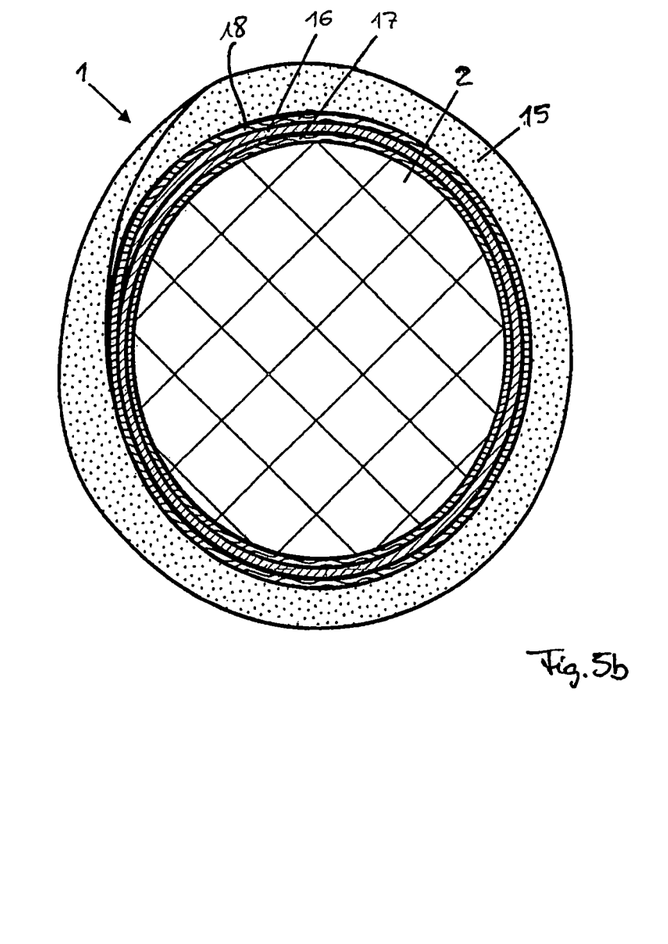
FIG. 5b is a view of a pressure cuff in accordance with FIG. 5a in a filled state.

The pressure cuff 1 can preferably, as is shown in FIGS. 5a and 5b, contain a first cuff part 15 that can be filled with the fluid, as well as a second cuff part 16 located between the first cuff part 15 and the extremity 2, which is designed in such a way that it avoids the formation of creases, in particular when filling the fluid into the first cuff part 15. The second cuff part 16 may in particular consist of a layer of a relatively stiff material (in relation to the substance from which the first cuff part 15 is formed), in particular a synthetic material, and, in its initial, unrolled form, be rolled up in a spiral shape, with overlapping ends. The second cuff part 16 is, in that respect, preferably formed in such an elastic, malleable way that its spiral shape can at least be bent upwards a bit, which may in particular be advantageous for placing the pressure cuff 1 on the extremity 2. Through the second cuff part 16, a transmission of the radial pressure on the entire contact area formed between the pressure cuff 1 and the extremity 2 generated by the first cuff part 15 when filling it with the fluid that is as uniform as possible can be achieved (cf. FIG. 5b). In addition, the restoring force of the elastically bent up second cuff part 16 may also ensure that the pressure cuff 1 is placed on the extremity 2 in a secure and narrow way, if the first cuff part 15 is not filled with fluid to an extent that a relevant radial pressure is exerted by it on the extremity 2 (cf. FIG. 5a).

In order to increase the comfort of the pressure cuff 1 for the wearer, the latter can, moreover, also include a third cuff part 17, which is located between the second cuff part 16 and the extremity 2. The third cuff part 17 can, in particular, consist of a soft, flexible material, for example fabric, and/or be formed as an enclosed (annular) cuff. A particular advantage of such a third cuff part 17 may be constituted by the latter being able to prevent a part of the surface of the extremity 2 from getting caught in the area of the overlapping ends of the second cuff part 17. In so far as the third cuff part 17 is additionally formed to be radially extendable, because it is elasticated, it can be ensured that this (together with the other cuff parts) can, by being extended, be pulled up onto the extremity 2 without any problem, however likewise (just like the second cuff part 16) does not thereafter form any creases when placed on the extremity 2.

A fourth cuff part 18 can, moreover, be provided for, which is placed between the first cuff part 15 and the second cuff part 16 and can be formed in line with the third cuff part 17. The fourth part of the cuff 18 can in particular prevent damage to the first part of the cuff 15 due to the loose ends of the second part of the cuff 16.

Such a pressure cuff is disclosed in International Patent Application PCT/EP2014/000340, the entire content of which is made the content of the present description by reference to it.

Two optical sensors are integrated into the pressure cuff, such as shown, for example, in FIG. 1. In the case of the preferred embodiment of the pressure cuff 1 with multiple cuff parts (cf. FIGS. 5a and 5b) the sensors are placed at the end of the second cuff part 16 facing the extremity 2, or, if a third cuff part 17 is provided for, at the corresponding end of such third cuff part 17.

Each of the sensors comprises an illuminant in the form of a light-emitting diode 4a, 4b (LED), as well as an adjacent detector in the form of a photodiode 5a, 5b (PD). By being placed underneath the pressure cuff 1, that is preferably largely transparent, the photodiodes 5a, 5b are already well protected from being irradiated by extraneous light. The respective arrangement of the photodiodes 5a, 5b between a central longitudinal axis 5 of the pressure cuff 1 aligned in a circumferential direction and the respective associated light-emitting diodes 4a, 4b in addition ensures that any light radiating at the edge under the pressure cuff 1 to the extent possible does not reach the photodiodes 5a, 5b. The light-emitting diodes 4a, 4b are connected in an antiparallel manner, in order to keep the number of connecting cables to a minimum.

The photodiodes 5a, 5b are connected in parallel, and electrically connected to an evaluation unit 7 of the device. Through being connected in parallel, both photodiodes 5a, 5b have the electrical effect of a single photodiode. Measuring signals which generate the photodiodes 5a, 5b due to light incidence, in principle go through the same receiving circuit. It is thereby achieved that a transient response for the measuring signals of the two photodiodes 5a, 5b is essentially the same.

Figure 2:
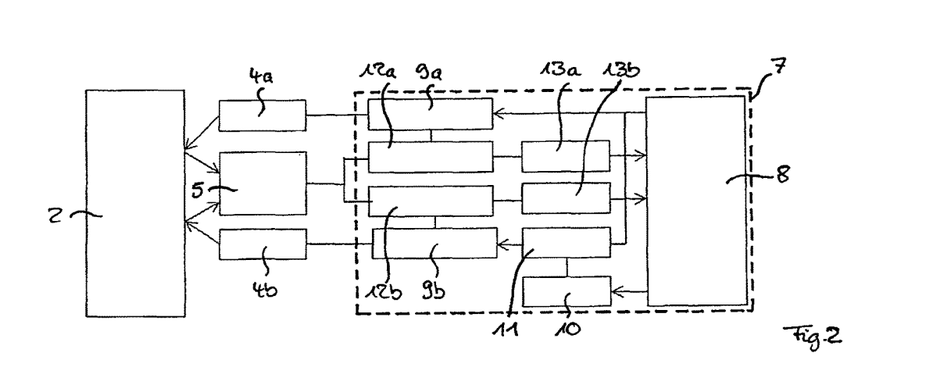
FIG. 2 is a functional diagram concerning the device from FIG. 1.

As an alternative to the embodiment shown here with two photodiodes 5a, 5b, connected in parallel, a photodiode 5 that is jointly used for both sensors can also be utilized (shown in FIG. 2 schematically). Such a joint photodiode 5 generates measuring signals due to light irradiation, which is based on light pulses that have been emitted by both light emitting diodes 4a, 4b. Such joint use is possible without any problem, due to the time offset defined, with which the two light emitting diodes 4a, 4b are activated, one after another. A joint photodiode 5 could, for example, be arranged centrally between the two light emitting diodes 4a, 4b.

In order to determine the pulse wave transit time, the two light-emitting diodes 4a, 4b are activated in pulsed form by the evaluation unit 7 (cf. FIG. 1), causing the latter to emit light pulses into the tissue located underneath the sensors, as well as the blood flowing through the artery 3 at the intervals specified by the activation. A part of the light is, in the process, reflected by the tissue and the blood, wherein a portion of it radiates into the respective associated or common photodiode 5, 5a or 5b. A respective ray of light, which is reflected by a blood corpuscle 14 into the photodiode 5a, 5b, is, for example, shown in FIG. 1. Such reflecting actually involves a large number of blood corpuscles 14, and also the tissue forming and surrounding the arterial wall. Since the tissue does, however, not change to a relevant extent on short notice, the portion of the light being reflected by the latter transpires to be the same portion in the case of measurement signals determined that follow on from one another at brief intervals, while changes (changing components in the area of the heart rate) are primarily attributable to the portion of the light reflected by the blood. Such changes are primarily due to the pressure waves caused by the heartbeat, which move through the artery 3 with the pulse wave velocity, leading to a cyclic, local bulging of the artery 3 caused by pressure, and, depending on the flow, changing the orientation and shape of the blood corpuscles.

As can be seen from FIG. 2, the evaluation unit 7 comprises a computing unit 8 and in each case a timer 9*a*, 9*b* for each of the light emitting diodes 4*a*, 4*b*. The light-emitting diodes 4*a*, 4*b* are activated in accordance with the parameters set by the computing unit 8 by means of the timer 9*a*, 9*b*. A delay element 11 controlled by a regulator 10 is additionally connected between the timer 9*b* of the second light-emitting diode 4*b* located upstream in relation to the direction of the flow of blood in the artery and the computing unit 8. The second light-emitting diode 4*b* is thus only activated by the delay element 11 with a time offset predetermined by the computing unit 8 after activating the first light-emitting diode 4*a*. The photodiode(s) 4*a*, 4*b* is/are connected with the computing unit via two integrators 12*a*, 12*b* and analog-to-digital converters 13*a*, 13*b*. The timers 9*a*, 9*b* shown in FIG. 2, the delay element 11, the regulator 10, the integrators 12*a*, 12*b* and the analog-to-digital converters 13*a*, 13*b* are functional elements, which can also be integrated into the computing unit 8, or their function can also be taken over by the computing unit 8.

A course of a measuring sequence carried out by means of both sensors, the total duration of which may, for example, amount to 1 ms, will run as follows. A dark current measurement is undertaken using the common photodiode, or the photodiode 5*a* associated with the first light-emitting diode 4*a*. This serves the purpose of being able to determine and calculate the measurement error owing to the radiation of extraneous light during a subsequent recording of the measurement signal with the first light-emitting diode 4*a* being activated. A pulse-like activation of the first light-emitting diode 4*a* will thereupon be performed, with an activation current (cf. FIG. 3: ILEDI), which leads to a light pulse being emitted by the first light-emitting diode 4*a*. A portion of the light that is emitted in the process is detected by the (associated) photodiode 5, 5*a* and converted into a corresponding measuring signal (1PD). Due to the transient response of the photodiode 5, 5*a* and the receiving circuit connected to it, the measuring signal is not set digitally, to either one of the states "existing" or "not existing" with an end value, but a relatively slow rise from zero (or the measuring signal defined as zero, determined in the dark current measurement) can be discerned (cf. FIG. 3). The pulse duration of the activation of the first light-emitting diode 4*a* is selected to be so short that it is switched off again even before the measuring signal of the (associated) photodiode 5, 5*a* has at all reached a steady state, and thus supplies a predominantly constant signal. Thus, a measuring signal, having reached a steady state, cannot serve as a measurement reading for the corresponding light pulse. Rather, the integral under the measuring signal curve is typically used over the period of the light pulse (the cross-hatched surface on the right in FIG. 3). It may, however, also be possible and advantageous to form the integral over the entire timespan in which the measuring signal is different from zero (approx. double the duration of a light pulse; the sum of the areas cross-hatched on the right and left-hand sides in FIG. 3). A measurement reading for the light pulse of the first light-emitting diode 4*a* observed, obtained in this way, is converted using the associated analog-to-digital converter 13*a*, and transmitted to the computing unit 8.

Figure 3:
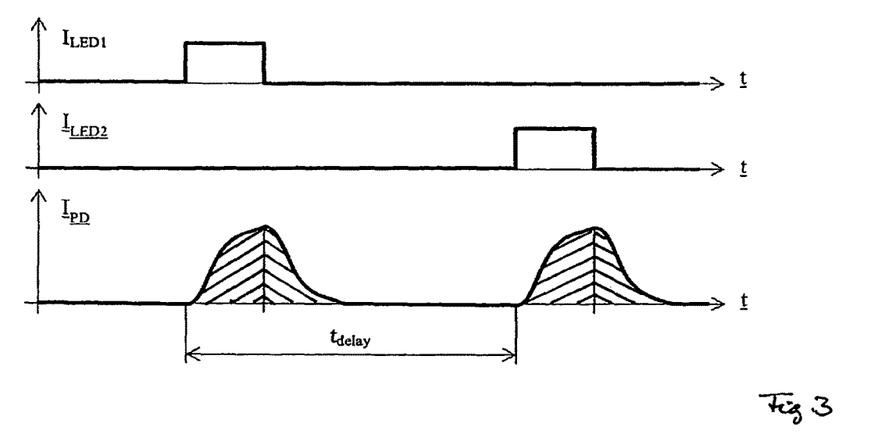
FIG. 3 is a graph showing the energizing of the two light-emitting diodes, as well as the resulting course of the measuring signal in a measurement sequence.

After a defined time offset (tdelay), which is set by the delay element 11, the second light-emitting diode 4*b* is activated accordingly in a pulsating manner. A measurement reading is obtained in line with the way it is obtained in the case of the first light-emitting diode 4*a*.

The two measurement readings determined within a measuring sequence, one for each of the sensors, are dependent upon the respective volumes in the case at hand, which are formed by the sections of the artery 3 located underneath the sensors. These volumes and thus the measurement readings, are changed in consequence of the pressure waves caused by the heartbeat traveling through the artery 3 at the pulse wave velocity. If a large number of corresponding measurement sequences are carried out directly after one another, a measurement value trend, and—in connection with the transfer function—a pulse curve form can always be derived from the measurement readings of each of the two sensors (cf. FIG. 4). These pulse curve forms may be largely identical following a standardization, however offset by the time offset (tdelay).

Figure 4:
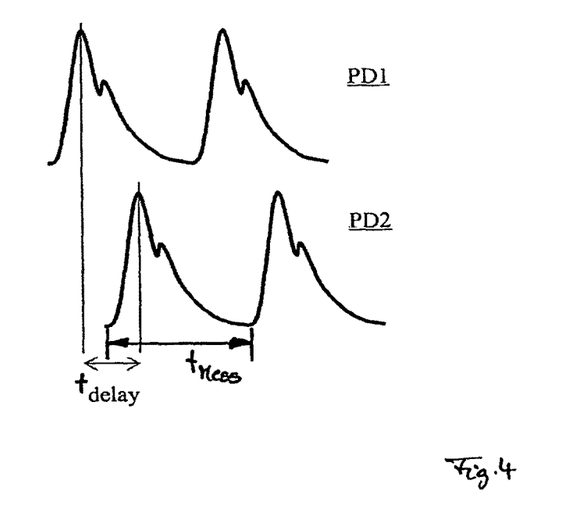
FIG. 4 is a graph showing two measurement progressions determined by means of the two sensors of the device.

In so far as the time offset between the activation of the two light-emitting diodes 4*a*, 4*b* is of such a nature that the measurement readings determined in a measurement sequence are identical, viewed relatively, i.e. essentially constitute the same point on the two standardized pulse curve forms, the time offset corresponds to the (pulse) transit time, which the pulse waves require for traveling from the first sensor to the second sensor. In connection with the known distance of the two sensors (in this respect the distance between the two sensors can be approximately used, e.g. of approx. 5 to 10 cm, in particular approx. 8 cm), the pulse wave velocity can be determined from the pulse wave transit time.

It is known that the pulse wave velocity is dependent upon the arterial blood pressure. To be specific, the pulse wave velocity is dependent upon the stiffness of the arterial vessel walls, which is, in turn, dependent upon pressure. When applied for a brief period of time with correspondingly minor changes (in the mean arterial pressure) the change in the pulse wavetransit time can in particular be considered inversely proportional to the change in the mean arterial pressure (MAP). In the event of greater changes occurring, a functional dependence can in any case still be assumed from the mean arterial pressure. Accordingly, the mean arterial pressure can be concluded via the pulse wave velocity determined.

The sensor-based mean arterial pressure determined can be transferred to a quantitative pulse curve form, via the transfer function, which is obtained using the result of a clamping pressure measurement. Thus, the blood pressure pattern can be determined continuously using the measuring signals, wherein it is stipulated to undertake a respective clamping pressure measurement at defined time intervals, in order to enable a re-calibration of the measuring signals or the blood pressure pattern derived therefrom.

Such a time interval, which may, for example, amount to approx. five minutes, accordingly comprises a large number of measuring procedures. Each measuring procedure (tMess) (at least) comprises determining a cycle of the measurement value trends of both sensors. Since the latter are synchronized with the heartbeat through the continuous phase regulation, the duration of one measuring procedure amounts to approx. 0.25 s to 2 s (in accordance with a heartbeat rate of 30 to 240, plus the time offset set, that only carries marginal weight, which corresponds to the pulse wave transit time and, at a sensor distance of approx. 8 cm amounts to approx. 6.75 to 10 ms).

The time offset, with which the second light-emitting diode 4*b* is activated after the first light-emitting diode 4*a* in every measuring sequence, is controlled at least once for every measuring procedure. In that respect, it is decided, for one or more measuring sequences of the measuring procedure that has just been performed, whether the corresponding measuring sequence(s) of the previous measuring procedure has/have led to substantially identical relative measurement readings. Should it be possible to ascertain any deviation, the time offset used with the previous measuring procedure is controlled accordingly. This controlled time offset is then taken as the basis for the measurement sequences of the new or one of these subsequent measuring procedures.

A method of ascertaining blood pressure in accordance with the present invention is typically not a diagnostic procedure. It does not permit any final diagnosis of a clinical picture, but serves to determine the operational reliability of the cardiovascular system of a test subject or patient. Any deviations from the blood pressure of a person recognized to be healthy determined, which may or may not be of a pathological nature, for example in the case of agitated test subjects, are, however, only starting points for any further diagnostic clarifications required.

LIST OF REFERENCE SIGNS

1 Pressure cuff
2 Extremity
3 Artery
4a Light-emitting diode of the first sensor
4b Light-emitting diode of the second sensor
5a Photodiode of the first sensor
5b Photodiode of the second sensor
6 Central longitudinal axis
7 Evaluation unit
8 Computing unit
9a Timer of the first sensor
9b Timer of the second sensor
10 Regulator
11 Delay element
12a Integrator of the first sensor
12b Integrator of the second sensor
13a Analog-to-digital converter of the first sensor
13b Analog-to-digital converter of the second sensor
14 Blood corpuscles
15 First cuff section
16 Second cuff section
17 Third cuff section
18 Fourth cuff section

The invention claimed is:

1. A method for determining blood pressure in a blood vessel, comprising the steps of:
   determining a pulse wave transit time using at least two sensors arranged at a defined distance from one another;
   determining the blood pressure from a change in the pulse wave transit time by a calibration based on a signal that is synchronous with pulse rate and without use of any further signal that is in proportion to the flow velocity.

2. The method in accordance with claim 1, wherein the calibration comprises calibrating the blood pressure determination using a clamping blood pressure measurement.

3. The method in accordance with claim 1, wherein the step of determining a pulse wave transit time is performed multiple times and the calibration is performed after multiple determinations of the pulse wave transit time.

4. The method in accordance with claim 3 wherein, if no clamping pressure measurement is performed, a holding clamping pressure is applied by means of a pressure cuff incorporating the at least two sensors.

5. The method in accordance with claim 1, wherein:
   light pulses are emitted in a direction of the blood vessel using an illuminant of the at least two sensors; and
   a portion of the light pulses reflected by blood in the blood vessel and/or a portion transmitted by the blood in the blood vessel is detected using a detector of the at least two sensors during a light detection.

6. The method in accordance with claim 5, wherein a time offset between an activation of the at least two sensors is controlled so that similar relative light detection measurement readings are achieved, which essentially show a same place in a comparable light detection measurement value trends in regard to a light detection measurement curve form.

7. The method in accordance with claim 6, wherein the time offset is determined based on characteristic values of light detection measurement trends.

8. The method in accordance with claim 7, wherein minimum and/or maximum values and/or values at points of maximum increase in the light detection measurement are used as characteristic values.

9. The method in accordance with claim 5, wherein a duration of the light pulses in comparison to phases of a drop in the light detection measurement readings is extended in phases of an increase in the light detection measurement readings.

10. The method in accordance with claim 9, wherein multiple light detections per light pulse are performed in phases of an increase.

11. The method in accordance with claim 9, wherein a duration of the light detection is extended in phases of an increase in the light detection measurement readings in comparison to the duration of the light detection in phases of a drop in the light detection measurement readings.

12. The method in accordance with claim 5, wherein a number of the light pulses per heartbeat is kept constant, depending upon the heart rate.

13. The method in accordance with claim 1, wherein in order to determine a light detection measurement reading, a maximum increase and/or a integral of the corresponding light detection measurement signal pattern is used.

14. A device for carrying out the method in accordance with claim 1, comprising:
   at least two sensors;
   a pressure cuff for performing a clamping pressure measurement; and
   an evaluation unit;
   wherein the at least two sensors are integrated into the pressure cuff.

15. A device in accordance with claim 14, wherein the sensors have a common detector or two detectors connected in parallel.

16. A device in accordance with claim 15, wherein the detector of a sensor is located between an illuminant of said sensor and a central longitudinal axis of the pressure cuff.

* * * * *